United States Patent [19]

Tomes et al.

US005773697A

[11] Patent Number: 5,773,697

[45] Date of Patent: Jun. 30, 1998

[54] GENETIC CONSTRUCTS AND METHODS FOR PRODUCING FRUITS WITH VERY LITTLE OR DIMINISHED SEED

[75] Inventors: Dwight T. Tomes, Cumming, Iowa; Bin Huang, Toronto, Canada; Paul D. Miller, Granger, Iowa

[73] Assignee: Pioneer Hi-Bred International, Inc., Des Moines, Iowa

[21] Appl. No.: 636,283

[22] Filed: Apr. 23, 1996

[51] Int. Cl.$^6$ .......................... C12N 15/29; C12N 15/82; A01H 4/00; A01H 5/00

[52] U.S. Cl. ............................... 800/205; 800/DIG. 19; 536/23.7; 536/24.1; 435/69.1; 435/172.3; 435/320.1

[58] Field of Search ........................... 800/205, DIG. 19; 536/23.7, 24.1; 435/320.1, 172.3, 69.1

[56] References Cited

U.S. PATENT DOCUMENTS

| | | | |
|---|---|---|---|
| 4,519,163 | 5/1985 | Bonner | 47/58 |
| 4,810,649 | 3/1989 | Sondahl et al. | 435/240.49 |
| 4,877,438 | 10/1989 | Lindow | 71/79 |
| 5,175,095 | 12/1992 | Martineau et al. | 435/69.1 |
| 5,177,011 | 1/1993 | Shewmaker et al. | 435/172.3 |
| 5,254,801 | 10/1993 | Dotson et al. | . |
| 5,420,034 | 5/1995 | Kridl et al. | 435/240.4 |
| 5,426,041 | 6/1995 | Fabijanski et al. | 435/172.3 |

FOREIGN PATENT DOCUMENTS

| | | | |
|---|---|---|---|
| WO 91/07295 | 7/1991 | WIPO | C12N 15/82 |
| WO 91/09957 | 7/1991 | WIPO | C12N 15/82 |
| WO 92/01799 | 2/1992 | WIPO | C12N 15/82 |

OTHER PUBLICATIONS

Stalberg et al. Deletion analysis of a 2S seed storage protein promoter of *Brassica napus* in transgenic tobacco. Plant Molecular Biology 23: 671–683, 1993.

Mihaly Czako et al., "Differential Manifestation of Seed Mortality Induced by Seed–Specific Expression of the Gene for Diphtheria Toxin A Chain in Arabidopsis and Tobacco", *Mol. Gen Genet*, (1992) 235:33–40.

van der Geest, Apolonia H.M., et al., "Cell Ablation Reveals That Expression from the Phaseolin Promoter is Confined to Embryogenesis and Microsporogenesis", *Plant Physiol.*, (1995) 109:1151–1158.

Koning, Ann et al., "Arrest of Embryo Development in *Brassica napus* Mediated by Modified *Pseudomonas aeruginosa* Exotoxin A", *Plant Molecular Biology* (1992) 18:247–258.

Sitbon, Folke et al. "Transgenic Tobacco Plants Coexpressing the *Agrobacterium tumefaciens* iaaM and iaaH Genes Display Altered Growth and Indoleacetic Acid Metabolism", *Plant Physiol* (1992) 99:1062–1069.

[Abstract 161] Nir, Canni Two Approaches to Genetically Engineered Parthenocarpy Rivka Barg, *Dept. Plant Genet*, The Volcani Center, Aro, Bet–Dagan 50250 Israel; Inst. Plant Genet., Slovak Acad Sci. Nitra 94902, Slovak Rep.

Vivekananda, Jeevalatha, "Horomonal and Environmental Regulation of the Carrot Lea–Class Gene Dc3", *Plant Physiol* (1992) 100:576–581.

Freiberg, "Tissue Culture Patent May 'Revolutionize' the Watermelon Industry" Looking for Commercial Partner, *AG Biotechnology News*, p. 6 May/Jun. 1991.

Compton, "A Simple Protocol for Micropropagating Diploid and Tetraploid Watermelon Using Shoot–Tip Explants", *Plant Cell. Tissue and Organ* Culture, 33:211–217, 1993.

*Primary Examiner*—Douglas W. Robinson
*Assistant Examiner*—Thomas Haas
*Attorney, Agent, or Firm*—Zarley, McKee, Thomte, Voorhees, & Sease

[57] ABSTRACT

The invention discloses a transgenic method for producing fruit with diminished or very little seeds or fruits with reduced seed number. It involves the temporal expression of a cytotoxic gene or combination of genes targeted toward arresting seed development at a time sufficiently after pollination that fruit development and maturation is normal while early enough in seed development that seed maturation per se is minimized. The invention also includes transgenic constructs, vectors, and methods for production of the fruit with diminished or very little seed bearing plants.

27 Claims, No Drawings

GENETIC CONSTRUCTS AND METHODS FOR PRODUCING FRUITS WITH VERY LITTLE OR DIMINISHED SEED

FIELD OF THE INVENTION

This invention relates generally to the field of plant olecular biology and in particular to transgenic plants, seeds, and tissues which have been genetically modified to create plants that when pollinated, produce seedless fruits and vegetables.

BACKGROUND OF THE INVENTION

Seedless fruits and vegetables have long been a goal of those in the field of produce. Benefits of such plants include the obvious appeal to consumers for ease in preparing and consuming such produce. Other benefits include a sweeter, fleshier fruit or vegetable, and an increase in edible portion as the seed cavity is absent or greatly reduced. Several advances have been made in this field, usually with topical application of hormones or with highly complex breeding procedures resulting in a triplex genotype.

For example, topical application of gibberellins has long been used for production of seedless grapes. This method usually requires a spraying procedure which is cumbersome, weather dependent, and must be timed correctly to occur immediately after pollination.

Another method requires a complex breeding procedure for production of seedless watermelons. The seedless condition in watermelon is almost always the result of the presence of three homologous complements per cell rather than the usual two, known as triploid. Seed development is arrested because of the unbalanced genome constitution of embryo and endosperm and irregular meiosis and gamete formation. The abnormal embryo formation causes the cessation of normal ovular development into a seed at an early stage. Typically seedless watermelons contain small edible white ovules similar to those in immature cucumbers.

These triploid seeds are produced by crossing male diploid (2X) lines containing 22 chromosomes per cell with female tetraploid (4X) lines containing 44 chromosomes per cell. The triploid genotype is produced by a 4n-2n cross, 3n seed is "normal" and is planted by growth. Triploid plants are true F1 hybrid so their production depends on development of diploid and tetraploid parental lines. For large scale commercial production of triploid seed, tetraploid and diploid parental lines are planted in mixed plots and allowed to cross pollinate. Triploid seed is produced only in melons on tetraploid plants that are fertilized with diploid pollen. Production fields of 3n watermelons have diploid pollinaters. Some 3n plants produce very little pollen, and the diploid pollen achieves inefficient pollination. The seed development is arrested post fertilization because of general unbalance. Thus an adequate supply of diploid and tetraploid seed must be available to produce large mixed stands. The major limitation to producing this type of seedless watermelon has been in the difficulty associated with producing sufficient seed for the tetraploid 4X parental lines.

Traditionally this is accomplished by application of colchicine. Colchicine inhibits mitotic spindle formation which leads to cells with various chromosome numbers. Tetraploids are produced by applying one drop per day of 0.2 to 0.4% aqueous colchicine to the diploid seedling apices. Often this treatment with colchicine results in death of the seedling or seed or produces aneuploids (cells with extra or missing chromosomes or polyploids).

Once a desirable cultivar is identified, chromosome number doubled, then it is self-pollinated to build up adequate seed. Tetraploid seed however has been very difficult to produce in large commercially useful quantities, largely due to the fact that tetraploids exhibit a high degree of self-sterility. Thus very few melons develop in a field of tetraploid plants. Seed production is more difficult in tetraploid parents produced in each self-pollinated melon. Ten or more years are typically required to increase seed of a new tetraploid line to commercially acceptable numbers.

U.S. Pat. No. 5,007,198 to Dennis Cray et al discloses a method for increasing production of tetraploid parental line for watermelon by overcoming the tetraploid cell sterility allowing for cloning of cultivar using unique tissue culture techniques. Generally, the method uses a tissue culture propagation method to "clone" the 4n parents by use of seedling merkstem as starting tissue for propagation of a watermelon tip in a petri dish filled with nutrients and growth regulators resulting in up to 15 shoots sprouting from a single tip. The shoots are in turn used to sprout even more cultures resulting in a geometric increase.

A transgenic method of creating seedless fruit is disclosed in World Patent WO91/09957. It involves a highly complex recombination excision system termed, "CRE-LOX". Generally the gene product of CRE produces a protein recombinase which acts at the specific LOX DNA sequence. Several recombination functions are disclosed with the most consistent being excision of the LOX DNA sequence. Seedless watermelons are hypothesized in the application to occur under the conditions involving transformation with the barnase gene derived from *Bacillus amyloiquefaciens*. Generally the female has a seed coat specific promoter (SC) :CRE:terminator the male has a SC promoter:barnase gene::lox::barnase gene:terminator. There are no phenotype changes in the two parents when propagated and in the seed production field the female seed parent has normal seed set because both genes are not functioning at the same time (seed coat is only maternal tissue). However in the F1 generation the maternal tissue will contain both genes. In this configuration, the constitution of the seed coat (F1 plant, F2 seeds) is SC promoter:barnase gene::-::barnase gene:terminator where ::-:: represents the point where the lox gene is excised making a functional toxin gene specific to the seed coat. In theory if the seed coat breaks down the development of the seed will be arrested because of lack of nutrient flow to the embryo.

No experimental data is disclosed and the success of the proposed protocol in development of actual seedless watermelon is nowhere shown.

Thus it can be seen from the foregoing that a need exists in the art for production protocols for seedless fruits and vegetables which are simple, straightforward and easily repeatable.

It is an object of the present invention to provide expression constructs which when expressed in a transgenic plant result in production of seedless fruits and vegetables.

It is yet another object of the invention to provide inbred parental lines which can be crossbred resulting in an F1 plant which will produce no seeds or a significant reduction in the amount of seeds present.

It is yet another object of this invention to provide plants, plant cells and plant tissues containing the expression constructs of the invention.

It is yet another object of the invention to provide vehicles for transformation of plant cells including viral or plasmid vectors in expression cassettes incorporating the genes and promoters of the invention.

It is yet another object of the invention to provide bacterial cells comprising such vectors for maintenance replication and plant transformation.

Other objects of the invention will become apparent from the description of the invention which follows.

SUMMARY OF THE INVENTION

The invention comprises the temporal expression of a cytotoxic gene or combination of genes targeted toward arresting seed development at a time sufficiently after pollination so that fruit development and maturation is normal while early enough in seed development that seed maturation per se is minimized.

In one embodiment the invention comprises a first DNA sequence encoding a first gene product which is capable of rendering a non-toxic substance cytotoxic to a cell of a plant which is critical to seed formation and/or function and a second DNA sequence encodes a second gene product which is a non-toxic substance or encodes a second gene product which is capable of converting a substance endogenous to a plant cell to a non-toxic substance, which can be converted by said first gene product to a cytotoxic substance.

The two gene combination makes possible the production of hybrid plants (F1) which will produce fruits or vegetables (F2) that will be seedless. Transgenic homozygous parental lines are maintained with each parent containing either the first or second recombinant DNA sequence operativley linked to a seed specific promoter. The two sequences come together only when the parental lines are crossed and result in a fully functional cytotoxic gene, the expression of which is timed with seed development. Preferably, the first DNA sequence encodes indole acetamide hydrolase (IamH), which converts Indole Acetamide to the native plant auxin Indole Acetic Acid (otherwise known as auxin gene 2) the second DNA sequence encodes indole acetamide synthase (IamS) which converts tryptophan to Indole Acetomide (otherwise known as auxin gene 1) and the first and second promoters are seed specific promoters. Overproduction of auxin in a tissue specific manner can result in localized toxicity to that tissue. Auxin overproduction tied to a pollen specific promoter has been used previously to produce male sterile plants, See U.S. Pat. No. 5,426,041 to Fabijanski incorporated herein by reference.

In another embodiment of the invention the first and second cytotoxic recombinant DNA sequences may be both transformed into the same plant which may then be vegetatively reproduced or cultivated to produce other such genetically identical plants.

DETAILED DESCRIPTION OF THE INVENTION

In the description that follows a number of terms are used extensively. The following definitions are provided in order to remove ambiguities in the intent or scope of their usage in the specification and claims, and to facilitate understanding of the invention.

As used herein the term fruit shall include any angiosperm plant which has its pollen and ovule producing organs in flowers; with ovules enclosed in an ovary, and after fertilization with each ovule developing into a seed while the ovary expands into a fruit. Any such fruit which is desirable of being produced in a seedless manner is encompassed by this definition. Further food sources traditionally considered vegetables but which are produced in this manner are also included such as tomatoes, peppers and the like.

A cytotoxic protein is one which disrupts normal cell functions.

A promoter is a DNA sequence that directs the transcription of a structural gene. Typically a promoter is located in the 5' region of a gene, proximal to the transcriptional start site of a structural gene.

A seed specific promoter is any promoter capable of regulating temporal expression at a time sufficiently after pollination that fruit development and maturation is normal but which is early enough in seed development that seed maturation is minimized. Such promoters as delineated herein include but are not limited to inducible promoters, seed specific promoters of either maternal, paternal or hybrid origin or any other promoter associated with a gene involved in seed production or development.

The term expression refers to biosynthesis of a gene product. Structural gene expression involves transcription of the structural gene into MRNA and then translation of the mRNA into one or more polypeptides.

A cloning vector is a DNA molecule such as a plasmid, cosmid or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically gene expression is placed under the control of certain regulatory elements including promoters, tissue specific regulatory elements, and enhancers. Such a gene is said to be "operably linked to" the regulatory elements.

A recombinant host may be any prokaryotic or eukaryotic cell that contains either a cloning vector or an expression vector. This term also includes those prokaryotic or eukaryotic cells that have been genetically engineered to contain the clone genes in the chromosome or genome of the host cell.

A transgenic plant is a plant having one or more plant cells that contain an expression vector. Plant tissue includes differentiated and undifferentiated tissues or plants, including but not limited to roots, stems, shoots, leaves, pollen, seeds, tumor tissue and various forms of cells and culture such as single cells, protoplas, embryos, and callus tissue. The plant tissue may be in plant or in organ, tissue or cell culture.

General Recombinant Techniques

Production of a genetically modified plant tissue expressing a structural gene under the control of regulatory promoters combines teachings of the present disclosure with a variety of techniques and expedients known in the art. In most instances alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural cytotoxic gene selection are other parameters which may be optimized to achieve desired plant expression as is known to those of skill in the art and taught herein.

The selection of an appropriate expression vector will depend upon the method of introducing the expression vector into host cells. Typically an expression vector contains (1) prokaryotic DNA elements coding for a bacterial replication origin and an antibiotic resistance marker to provide for the growth and selection of the expression vector in a bacterial host; (2) DNA elements that control initiation of transcription such as a promoter; (3) DNA elements that control the processing of transcripts such as transcription termination/polyadenylation sequence; and (4) a reporter gene that is operably linked to the DNA elements to control transcription initiation. Useful reporter genes include β-glucuronidase, β-galactosidase, chloramphenicol acetyl transferase, luciferase, and the like. Preferably the reporter gene is either β-glucuronidase (GUS) or luciferase.

The general descriptions of plant expression vectors and reporter genes can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.).

Expression vectors containing genomic or synthetic fragments can be introduced into protoplast or into intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition Sprague et al. (Eds. pp. 345–387) American Society of Agronomy Inc. et al. 1988.

Methods of introducing expression vectors into plant tissue include the direct infection or co-cultivation of plant cell with Agrobacterium tumefaciens, Horsch et al., Science, 227:1229 (1985). Descriptions of agrobacterium vector systems and methods for agrobacterium-mediated gene transfer provided by Gruber, et al. supra.

Useful methods include but are not limited to expression vectors are introduced into plant tissues using a direct gene transfer method such as microprojectile-mediated delivery, DNA injection, electroporation and the like. More preferably expression vectors are introduced into plant tissues using the microprojectile media delivery with the biolistic device.

The invention comprises use of these types of transformation procedures to generate transgenic plants which bear seedless fruit. A construct comprising a cytotoxic gene operably linked to a seed specific promoter is introduced to said plant. The cytotoxic gene can be a single gene product or a combination of genes.

In a preferred embodiment the invention comprises use of a pair of genes which, when expressed together create a toxic gene product. This can allow for hybrid plant or seed production, once transgenic inbred parental lines have been established. For this embodiment the invention comprises a first DNA sequence encoding a first gene product which is capable of rendering a non-toxic substance cytotoxic to a cell of a plant which is critical to seed formation and/or function and a second DNA sequence encodes a second gene product which is a non-toxic substance or encodes a second gene product which is capable of converting a substance endogenous to a plant cell to a non-toxic substance.

It is desirable to have the first DNA sequence and second DNA sequence in homozygous state which may require more than one transformation event to create each parental line, requiring transformation with a first and second recombinant DNA molecule both of which encode the same gene product.

Preferably, the first recombinant DNA molecule and second recombinant DNA molecule are located on opposite chromatids of the same chromosome pair and most preferably on opposite chromatids of the same chromosome pair at the same genetic locus such that segregation of the first and second recombinant DNA molecules occurs during meiosis and the chance of recombination of the first and second recombinant DNA molecules to the same chromatid during meiotic crossing over is substantially reduced.

The methods of the invention described herein may be applicable to any species of seed-bearing plant, the fruit or vegetable of which is edible or within which it is desirable to make seedless for nuisance or other reasons. Fruits and vegetable plants which can be made seedless according to the methods of the invention include but are not limited to include, melons such as cantaloupe, honeydew and watermelon, and musk melon, berries such as strawberries, and blueberries, peppers such as green peppers, red bell peppers, yellow peppers, tomatoes, oranges, plums, alfalfa, squash, eggplant, sweetcorn, peas, cotton, avacados, mangos, papayas, nectarines, apples, grapefruit, lemons, limes, tangerines, pears and peaches. The methods of the invention will be illustrated below with reference to particular embodiments.

As herein before mentioned the first DNA sequence may encode a first gene product which is capable of rendering a non-toxic substance cytotoxic to a cell of a plant which is critical to seed formation and/or function and the second DNA sequence may encode a second gene product which is the non-toxic substance or encode a second gene product which is capable of converting a substance endogenous to a plant cell to said non-toxic substance.

A cell and/or tissue of a plant which is critical to seed formation and/or function includes cells and/or tissues that are instrumental in the development or seeds, including cells and/or tissues from which seeds develop, cells and/or tissues which form part of the seed coat, endosperm or embryo or other female structure in which seed develops (e.g. ovules), while not disrupting the maturation of the ovary into fruit or vegetable.

The first DNA sequence may be any identifiable DNA sequence encoding gene products which are capable of rendering a non-toxic substance cytotoxic to a cell of a plant which is critical to seed formation and/or function. Examples of such a DNA sequence includes a DNA sequence which encodes indole acetamide hydrolase (IamH) (Auxin gene 2) which converts naphthalene acetamide to the plant growth regulator alpha naphthalene acetic acid (NAA) (Auxin gene 2) which converts indole acetamide to indole acetic acid (IAA) which is a plant growth regulator. One source of the enzyme IamH is the bacterium *Agrobacterium tumefaciens* (Inze, D., et al, 1984, Mol. Gen. Genet. 194:265–74 and Koncz, C. and Schell, J., 1986, 204:383–396 re pPCV 311 plasmid derivative). Another source of an enzyme that is genetically equivalent to IamH is the gene coding for indole acetamide hydrolase from *Pseudomonas savastanoi* (Follin et al. (1985) Mol. Gen. Genet. 201:178–185). Yet another source is U.S. Pat. No. 5,426,041. Other such cytotoxic genes include DAM methylase, Diphtheria toxin or any other protein which disrupts normal cell function.

The first DNA sequence may also encode a gene product which is capable of rendering a non-toxic substance which is a protoxin cytotoxic to a cell of a plant that is critical to seed formation and/or function. A protoxin has been identified which is inactive against plants but upon enzymatic conversion becomes cytotoxic. (Dotson, S. B. and G. M. Kishore, Isolation of a Dominant Lethal Gene with Potential Uses in Plants In The Genetic Dissection of Plant Cell Processes 1991).

The second DNA sequence may encode a second gene product which is the non-toxic substance or encode a second gene product which converts a substance which is endogenous to a plant cell into the non-toxic substance. For example, a cell may contain a DNA sequence which encodes IamH (Auxin gene 2) (which converts indole acetamide to cytotoxic levels of indole acetic acid), and a DNA sequence which encodes IamS (Auxin gene 1). IamS converts tryptophan which is generally endogenous to plant cells, to indole acetamide which in turn is converted by IamH to cytotoxic levels of indole acetic acid. One source of the enzyme IaMS is the T-DNA gene 1 from the bacterium *Agrobacterium tumefaciens* (Inze, D., et al. 1984, Mol. Gen. Genet. 194:265–74). Another source of an enzyme that is functionally equivalent to IamS is the gene coding for tryptophan 2-mono-oxygenase from Pseudomonas savastanoi (Follin et al. (1985) Mol. Gen. Genet. 201:178–185). Yet another source is U.S. Pat. No. 5,426,041. The second DNA sequence may also encode non-toxic substances such as the above mentioned protoxin.

In a single gene embodiment the cytotoxic gene used is selected from a group of genes encoding products that disrupt normal functioning of cells. There are many proteins that are toxic to cells when expressed in an unnatural situation. Examples include the genes for the restriction enzyme EcoRI [Barnes and Rine, *Proc. Natl. Acad. Sci. USA* 82:1354–1358 (1985)], diphtheria toxin A[Yamaizumi et al., *Cell* 15:245–250 (1987)], streptavidin [Sano and Cantor, *Proc. Natl. Acad. Sci. USA* 87:142–146 (1990)], and barnase [Paddon and Hartley, *Gene* 53:11–19 (1987)].

The promoters used in the methods of the invention may be a seed specific promoter, an inducible promoter or a constitutive promoter.

The seed-specific promoter used is selected from the group of promoters known to direct expression in the embryo and/or the endosperm of the developing seed, most desirably in the endosperm. One set of examples of seed-specific promoters include but are not limited to the promoters of seed storage proteins. The seed storage proteins are strictly regulated, being expressed almost exclusively in seeds in a highly tissue-specific and stage-specific matter [Higgins et al., *Ann. Rev. Plant Physiol.,* 35:191–221 (1984); Goldberg et al., *Cell* 56:149–160 (1989)). Also, different seed storage proteins may be expressed at different stages of seed development and in different parts of the seed.

Other examples include maternal tissue promoters such as seed coat, pericarp and ovule. There are numerous examples of seed-specific expression of seed storage protein genes in transgenic dicotyledonous plants. These include genes from dicotyledonous plants for bean β-phaseolin [Sengupta-Goplalan et al., *Proc. Natl. Acad. Sci. USA* 82:3320–3324 (1985) and Hoffman et al., *Plant Mol. Biol.* 11:717–729 (1988], bean lectin [Voelker et al., *EMBO J* 6:3571–3577 (1987)], soybean lectin [Ocamuro et al., *Proc. Natl. Acad. Sci. USA* 83:8240–8344 (1986)], soybean kunitz trypsin inhibitor [Perez-Grau and Goldberg *Plant Cell* 1:1095–1109 (1989)], soybean β-conglycinin [Beachy et al., *EMBO J* 4:3047–3053 (1985), Barker et al., *Proc. Natl. Acad. Sci.* 85:458–462 (1988), Chen et al., *EMBO J* 7:297–302 (1988), Chen et al., *Dev. Genet.* 10:112–122 (1989), Naito et al., *Plant Mol. Biol.* 11:683–695 (1988)], pea vicillin [Higgins et al., *Plant Mol. Biol.* 11:109–123 (1988)], pea convicillin (Newbigin et al., *Planta* 180:461(1990)], pea legumin [Shirsat et al., *Mol. Gen. Genetics* 215:326 (1989)], rapeseed napin [Radke et al., *Theor. Appl. Genet.* 75:685–694 (1988)], as well as genes from monocotyledonous plants such as for maize 15-kd zein [Hoffman et al., *EMBO J* 6:3213–3221 (1987)], barley β-hordein [Marris et al., *Plant Mol. Biol.* 10:359–366 (1988)], and wheat glutenin [Colot et al., EMBO J 6:3559–3564 (1987)]. Moreover, promoters of seed-specific genes operably linked to heterologous coding regions in chimeric gene constructions also maintain their temporal and spatial expression pattern in transgenic plants. Such examples include *Arabidopsis thaliana* 2S seed storage protein gene promoter to express enkephalin peptides in *Arabidopsis* and *Brassica napus* seeds [Vandekerckhove et al., *Bio/Technology* 7:929–932 (1989)], bean lectin and bean β-phaseolin promoters to express luciferase [Riggs et al., *Plant Sci.* 63:47–57 (1989)], and wheat glutenin promoters to express chloramphenicol acetyl transferase [Colot et al., *EMBO J* 6:3559–3564 (1987)]. Promoters highly expressed early in endosperm development are most effective in this application. Of particular interest is the promoter from the a' subunit of the soybean β-conglycinin gene [Walling et al., *Proc. Natl. Acad. Sci. USA* 83:2123–2127 (1986)] which is expressed early in seed development in the endosperm and the embryo.

A seed specific promoter is a DNA sequence which regulates the expression of a DNA sequence selectively in the cells/tissues of a plant critical to seed formation and/or function and/or limits the expression of such a DNA sequence to the period of seed formation in the plant. Any identifiable seed or embryo specific promoter may be used in the methods of the present invention.

Other promoters which are seed or embryo specific and are useful in the method so the invention include the Phaseolin promoter described in U.S. Pat. No. 5,504,200 to Mycogen which is hereby incorporated by reference. The patent discloses the gene sequence and regulatory regions for phaseolin, a protein isolated from *P. vulgaris*. The phaseolin protein is highly regulated and the gene encoding the protein is expressed only while the seed is developing within the pod, and only in tissues involved in seed generation.

Another such promoter is the Napin promoter described in U.S. Pat. No. 5,110,728 to Calgene which is also incorporated herein by reference. The patent describes and discloses the use of the napin promoter in directing the expression to seed tissue of an acyl carrier protein to enhance seed oil production.

Other such promoters includes the DC3 promoter form carrots which is early to mid embryo specific and is disclosed at Plant Physiology, Oct. 1992 100(2) p. 576–581, "Hormonal and Environmental Regulation of the Carrot Lea-class Gene Dc 3". Another is disclosed at Plant Mol. Biol., April 1992, 18(6) p. 1049–1063, "Transcriptional Regulation of a Seed Specific Carrot Gene, DC 8". Other useful promoters include any promoter which can be derived from a gene whose expression is maternally associated with the embryo and or endosperm or late pollen formation.

The preferred promoters may be used in conjunction with naturally occurring flanking coding or transcribed sequences of the seed specific genes or with any other coding or transcribed sequence that is critical to seed formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to seed formation and/or function.

Additionally regions of one promoter may be joined to regions from a different promoter in order to obtain the desired promoter activity resulting in a chimeric promoter. Synthetic promoters which regulate gene expression to seed development may also be used.

The first promoter or the second promoter used in the method of the invention may be an inducible promoter. An inducible promoter is a promoter that is capable of directly or indirectly activating transcription of a DNA sequence in response to an inducer. In the absence of an inducer the DNA sequence will not be transcribed. Typically the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 KD heat shock promoter of D. melanogaster (Freeling, M., Bennet, D. C., Maize ADN 1, Ann. Rev. of Genetics 19:297–323) and the alcohol dehydrogenase promoter which is induced by ethanol (Nagao, R. T., et al., Miflin, B. J., Ed. Oxford Surveys of Plant Molecular and Cell Biology, Vol. 3, p. 384–438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

In a preferred embodiment the promoter is one which is seed coat specific, one which is expressed only in maternal tissue such as the a' subunit of β-conglycinin of soybean (a'-β- C6) which is highly expressed in early seed development i the endosperm and embryo described in *J. Biol. Chem.* 261:9228 (1986), incorporated herein by reference.

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl=2-chloro-4-(trifluoromethyl)-5-thiazolecarboxylate (common name: flurazole). In addition a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The first or second promoter may be a constitutive promoter. A constitutive promoter is a promoter that functions in all, many, or a variety of cell types including cells/tissues critical to pollen formation and/or function. An example of such a constitutive promoter is CaMV 35S or Super mass or HP 101 which has been isolated from *Brassica napus*.

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the MRNA coding for the NPT II gene by Northern blot analysis in RNA from the tissue of the transformed plant. Transformed plant cells thus selected can be induced to differentiate into plant structures which will eventually yield whole plants. It is to be understood that a selection marker gene may also be native to a plant.

A recombinant DNA molecule containing any of the DNA sequences and promoters described herein may be integrated into the genome of the male sterile plant or second plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, Science 208:1265) and gemini viruses (Goodman, R. M., 1981, *J. Gen Virol.* 54:9) as vectors has been suggested but by far the greatest reported successes have been with *Agrobacteria sp.* (Horsch, R. B., et al, 1985, *Science* 227:1229–1231). Methods for the use of *Agrobacterium* based transformation systems have now been described for many different species. Generally strains of bacteria are used that harbor modified versions of the naturally occurring Ti plasmid such that DNA is transferred to the host plant without the subsequent formation of tumors. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets from Agrobacterium mediated transformation as described specifically for members of the Brassicaceae. These include thin cell layers (Charest, P.J., et al, 1988, *Theor. Appl. Genet.* 75:438–444), hypocotyls (DeBlock, M., et al, 1989, *Plant Physiol.* 91:694–701), leaf discs (Feldman, K. A., and Marks, M. D., 1986, *Plant Sci.* 47:63–69), stems (Fry J., et al, 1987, *Plant Cell Repts.* 6:321–325), cotyledons (Moloney M. M., et al, 1989, *Plant Cell Repts.* 8:238–242) and embryoids (Neuhaus, G., et al, 1987, *Theor. Appl. Genet.* 75:30–36). It is understood, however, that it may be desirable in some crops to choose a different tissue or method of transformation.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

Other methods that have been employed for introducing recombinant molecules into plant cells involve mechanical means such as direct DNA uptake, liposomes, electroporation (Guerche, P. et al, 1987, *Plant Science* 52:111–116) and micro-injection (Neuhaus, G., et al, 1987, *Theor. Appl. Genet.* 75:30–36). The possibility of using microprojectiles and a gun or other devise to force small metal particles coated with DNA into cells has also received considerable attention (Klein, T. M. et al., 1987, *Nature* 327:70–73).

It is contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

As indicated above, it may be desirable to produce plant lines which are homozygous for a particular gene. In some species this is accomplished rather easily by the use of anther culture or isolated microspore culture. This is especially true for the oil seed crop *Brassice napus* (Keller and Armstrong, Z. flanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

A number of different ways of producing the toxic molecule specifically in seed can be envisioned. In all approaches, at least one step in the production of the cytotoxic molecule has to take place specifically within the seed, or endosperm or seed coat. For instance, it is possible to use a constitutively expressed IamS (Auxin gene 1) gene in a plant and to subsequently cross that plant with a plant that contains the IamH (Auxin gene 2) gene under the control of a seed specific promoter such that IAM is produced in all cells of the plant, but the growth regulator IAA is produced only in seed cells due to the action of the seed specific IamH gene. Conversely, it is possible to have IamH constitutively expressed in a plant, and cross this plant with a plant that contains a seed specific promoter driving the IamS gene. In this situation, the growth regulator IAA is only produced in seed cells. In several embodiments both the IamH gene and the IamS gene are placed under the control of seed specific promoters and preferably using the same seed specific promoter or a seed specific promoter whose expression substantially overlaps that of the other to each independently drive the expression of these two genes. Additionally, by linking the IamH gene to a selectable agent such as a herbicide, hybrid plant production is greatly facilitated.

Any number of genes could be used to carry out the process and methods of the invention providing that the 5 simultaneous production of one or more enzymatic or synthetic activities specifically in seed leads to the production of a substance which is toxic or inhibitory to normal seed production or specifically interferes with seed coat or endosperm development. This implies that one or more of these activities could be constitutive in the plant, but that the final combination of all enzyme activities be limited to seed.

As can be seen, several combinations of cytotoxic genes and seed development specific promoters are contemplated within the scope of the invention.

A highly desirable seedless system is one in which fully fertile F1 seed develops, that can then be grown into plants that produce only seedless fruit. This system is economically favorable in that for each cross pollination, a large number of seedless fruits result: the number of F1 seed from one cross X the number of fruits produced on an F1 plant. Also incorporated in this scheme are the advantages of growing a hybrid crop, including the combining of more valuable traits and hybrid vigor. This is accomplished in the same manner as described above except that the cytotoxic gene is expressed from a seed coat-specific promoter. The seed coat is the outgrowth of the integuments, a strictly maternal tissue. Therefore the hybrid cross that brings the disruption gene 1 together with the gene 2 does not involve this seed coat tissue. The seed coat of the F1 seed has either gene1 or gene 2, depending on which is used as the female parent, and thus F1 seed develop normally. After the F1 seed gives rise to a fruit-bearing F1 plant, all vegetative cells (including seed coat cells) inherit both gene 1 and gene 2 from the embryo. Thus the seed coat of the F1 plant has an activated cell disruption gene.

The seed coat is an essential tissue for seed development and viability. When the seed is fully matured, the seed coat serves as a protective layer to inner parts of the seed. During seed development, the seed coat is a vital nutrient-importing tissue for the developing embryo. The seed is nutritionally "parasitic" to the mother plant. All raw materials necessary for seed growth must be imported. In seeds of dicotyledonous plants, the vascular tissue enters the seed through the funiculus and then anastamoses in the seed coat tissue. There is no vascular tissue connection or plasmodesmata linkage between the seed coat and the embryo. Therefore, all nutrient solutes delivered into the developing seed must be unloaded inside the seed coat and then move by diffusion to the embryo. Techniques have been developed to study the nutrient composition in the seed coat [Hsu et al., *Plant Physiol.* 75:181 (1984); Thorne & Rainbird, *Plant Physiol.* 72:268 (1983); Patrick, *J. Plant Physiol.* 115:297 (1984); Wolswinkel & Ammerlaan, *J. Exp. Bot.* 36:359 (1985)], and also the detailed cellular mechanisms of solute unloading (Offler & Patrick, *Aust. J. Plant Physiol.* 11:79 (1984); Patrick, *Physiol. Plant* 78:298 (1990)]. It is obvious that the destruction of this vital nutrient-funnelling tissue causes seed abortion.

EXAMPLE 1

Several vectors were constructed according to the methods of the invention:

Gene1—pal 1425 (Bp 4 promoter +gene 1)

Gene2—pal 1426 (Bp 4 promoter +gene2)

The vectors were transformed according to Moloney et al., 1989, Pl. Cell Reports 8:238–242.

Seed was grown from each event as well as crossed made with each event. Once the plants flowered and tried to set seed, the pods were observed to be empty, in plants with Gene1 and Gene 2 as well as plants with Gene1 alone.

EXAMPLE 2

Several vectors have been made according to the invention and include
Supermass:PAT:PIN::DC3:GENE1–GENE2:PIN
Supermass:PAT:PIN::Napin:GENE1–GENE2:PIN
Supermass:PAT:PIN:Phaseolin:GENE1–GENE2:PIN The selectable marker for these vectors is the Supermass promoter operably linked to the PAT gene which conditions resistance to bialaphos (a herbicide), and the PIN II terminator (a polyadenylation signal). The three promoters for GENE1–GENE2 are all seed specific and should result in toxicity to seed development. The degree of inhibition of seed development will depend on when and where the promoters function. The primary transgenic events should show segregation in seed, and an expected phenotype is 3:1 ratio of non-filled seed to normal seed.

EXAMPLE 3

An early objective is to prove in principal that Gene1:Gene2 under the control of a seed specific promoter is capable of arresting seed development without adversely affecting fruit development, i.e. the gene(s) act in a tissue specific and cell autonomous manner. Melon is the choice for plant species because of short cycle time and relatively low greenhouse space requirements.

Plant expression vectors in which both Gene 1 and Gene 2 are placed under the control of either the DC3, napin, or phaseolin promoters will be used to test tissue and temporal specificity i.e. early seed development in melon. An expected phenotype would be T0 transgenics that produce fruit that has 75% aborted seeds when selfed or 50% aborted seeds when crossed with a wild type plant. Control plants which have been regenerated from tissue culture will be compared for aborted seed % to assure that the phenotype is not the result of other factors. Molecular analysis of individual seed will also confirm the presence of transgenes and cosegregation of aborted versus normal seeds.

In addition to functional evaluation of the toxicity of Gene1:Gene2, additional promoter evaluation can be done with the cytochemical gus marker and various seed specific promoters. It is likely that existing promoters will require modification or additional promoters will need to be isolated (see below) which have tissue and temporal expression compatible with the needs of this application.

EXAMPLE 4

Evaluation of Gene 1:Gene2 for Hybrid Seed Production Systems

Two systems will be evaluated for efficacy of hybrid seed production. The first is using a embryo specific promoter-:gene such as DC3::Gene 1 in the male and DC3::Gene 2 in the female parent. Both parents should produce seed normally when selfed or increased for seed production. However, abnormal floral phenotype has been observed with some combinations of anther specific promoters and Gene 1 in Brassica (Arnoldo, 1995, August monthly report, Canola Transformation). The degree of phenotypic abnormality will depend on the specific promoter, although the promoters 20 suggested should have much less phenotypic pertubation than those under the control of constituitive promoters (Sitbon, et al. 1992, "Transgenic Tobacco Plants Coexpressing the Agrobacterium Tumefaciens IAAM and IAAH Genes Display Altered Growth and Indoleacetic Acid Metabolism", *Plant Physiol.* 99:1062–1069; Klee et al 1987, "The Effects of Overproduction of Two *Agrobacterium Tumefaciens* T-DNA Auxin Biosynthetic Gene Products in Transgenic Petunia Plants", *Genes Dev.* 1:86–96). Both phenotypic and molecular analysis of seed set in the component parental combinations should verify the nature of seed maturation in both parental combinations.

A possible difficulty with this approach of hybrid seed production is that both Gene 1 and Gene 2 will be potentially expressed in the female parent used for seed production. The embryo is diploid and seed specific and if expression of component genes are expressed from equal contributions of male and female gametes the female parent in the seed production block will be seedless. An alternative of this approach would be releasing a hybrid which is homozygous for Gene2 and is either male sterile or gynoecious. A pollen donor containing Gene1 would also be supplied which would pollinate the male sterile hybrid containing Gene2. All fruit obtained from the hybrid would be "seedless".

Another alternative of this method would be repressing the transcriptional activity of Gene 1 in the female by using an inducible promoter. The Lex A gene (Brent and Ptashne, 1985, "A Eukaryotic Transcriptional Activator Bearing the DNA Specificity of a Prokaryotic Repressor", *Cell,* 43:729–736) is one such useful promoter. Gene 1 would normally be expressed in the female except during seed production of the hybrid in which the "inducer" is used to repress the gene. Thus seed production would be 'normal' while the F1 hybrid sold to growers would be seedless.

An approach compatible with conventional hybrid seed production is placing both Gene 1 and Gene 2 under the control of a seed coat specific promoter. Because the seed coat is a maternal origin, the female hybrid seed parent would not express the seedless phenotype when crossed with a male containing Gene 2 since the maternal tissue would only express Gene 1. The genetic constitution of the F1 embryo contains both Gene 1 and Gene 2, and in the growers field both would be expressed in the maternal tissue and would have seedless phenotype.

The technique of differential display using Rt-PCR could be used to advantage to selectively isolate message produced in seed coat tissue compared to both embryo specific tissue and fruit specific tissue. Such a technique has been used in several applications including isolation of cancer genes and in isolation of genes related to fruit ripening in tomato (Oh et al, 1995, "A Modified Procedure for PCR-Based Differential Displan and Demonstration of use in Plants for Isolation of Genes Related to Fruit Ripening", *Plant Mol. Rpt.,* 13:70–81.

What is claimed is:

1. An expression construct for production of transgenic plants that will produce fruit with seed of a diminished size or very little number of seed comprising:
   a recombinant gene or combination of genes which encode upon expression a cytotoxic protein; and
   a seed specific promoter operably linked to said gene or genes.

2. The expression construct of claim 1 wherein said combination of genes includes:
   a first DNA sequence which encodes a first gene product which is capable of rendering a non-toxic substance cytotoxic to a cell of a plant; and
   a second DNA sequence which encodes a second gene product which is a non-toxic substance or encodes a second gene product which is capable of converting a substance endogenous to a plant cell to a non-toxic substance, said nontoxic substance one which is made cytotoxic by said first gene product.

3. The expression construct of claim 2 wherein said first DNA sequence encodes indole acetamide hydrolase (IamH), and wherein said second DNA sequence encodes indole acetamide synthase (IamS).

4. The expression construct of claim 1 wherein said cytotoxic gene encodes DAM methylase.

5. The expression construct of claim 1 wherein said promoter is a maternal tissue promoter.

6. The expression construct of claim 1 wherein said promoter is selected from the group consisting of:
   the napin promoter, the phaseolin promoter, and the DC3 promoter.

7. The expression construct of claim 1 wherein said promoter is an inducible promoter.

8. An expression construct for the production of a transgenic parental line which when crossed with a second parental line containing a DNA sequence which encodes a second gene product which is a non-toxic substance or encodes a second gene product which is capable of converting a substance endogenous to a plant cell to a non-toxic substance, said nontoxic substance one which is made cytotoxic by said first gene product, will produce an F1 plant which will develop fruit with seed of a diminished size or very little number of seed comprising:
   a DNA sequence which encodes a first gene product which is capable of rendering a non-toxic substance cytotoxic to a cell of a plant, said first gene product operably linked to a seed specific promoter.

9. An expression construct for the production of a transgenic parental line which, when crossed with a second parental line which contains a DNA sequence regulated by a seed specific promoter which encodes a first gene product which is capable of rendering a non-toxic substance cytotoxic to a cell of a plant, which will produce an F1 plant which will develop fruit with seed of a diminished size or very little number of seed comprising:
   a DNA sequence which encodes a second gene product which is a non-toxic substance or encodes a second gene product which is capable of converting a substance endogenous to a plant cell to a non-toxic substance, said nontoxic substance one which is made cytotoxic by said first gene product.

10. A nucleic acid vector comprising the expression constructs of claim 1, 8 or 9.

11. The vector of claim 10 wherein said vector is a cloning vector.

12. The vector of claim 10 wherein said vector is an expression vector.

13. The vector of claim 10 further comprising a marker gene for selection of transformed cells.

14. The vector of claim 12 wherein said marker gene is selected from the group consisting of an ampicillin resistance gene, a tetracycline resistance and a hygromycin resistance gene.

15. The vector of claim 10 further comprising a polyadenylation signal.

16. A prokaryotic or eukaryotic host cell transformed with the nucleic acid vector of claim 10.

17. A transgenic plant comprising a plant cell or ancestor thereof which has been transformed with the vector of claim 10.

18. A method of producing a hybrid seed which, will produce a plant which, when pollinated will produce fruit with seed of a diminished size or very little number of seed comprising:
   pollinating a parent plant which has been transformed or which ancestor thereof has been transformed with a first DNA sequence which encodes a first gene product which is capable of rendering a non-toxic substance cytotoxic to a cell of a plant said DNA sequence operably linked to a maternal tissue specific promoter; and
   with a second parent plant which has been transformed or whose ancestor has been transformed with a second DNA sequence which encodes a second gene product which is a non-toxic substance o codes a second gene product which is of converting a substance endogenous to a plant cell to a non-toxic substance, said DNA sequence operably linked to a maternal tissue specific promoter, and said nontoxic substance one which is made cytotoxic by said first gene product.

19. The method of claim 18 wherein said maternal tissue specific promoter is a seed coat specific promoter.

20. A hybrid seed produced by the method of claim 18.

21. A fruit with diminished or very little seed produced by a plant which contains a DNA sequence encoding a cytotoxic protein expressed during seed development.

22. A method of producing fruit with diminished or very little seed comprising:

transforming an angiosperm plant cell with a DNA sequence which encodes a cytotoxic gene operably linked to a seed specific promoter;

generating a plant from said transformed cell; and allowing said plant to be pollinated so that seed development is initiated and then halted without interrupting fruit set.

23. The method of claim 22 wherein said plant is a melon plant.

24. The method of claim 22 wherein said DNA sequence encodes indole acetamide hydrolase (IamH), and indole acetamide synthase (IamS).

25. The method of claim 22 wherein said promoter is selected from the group consisting of:

the napin promoter, the phaseolin promoter, and the DC3 promoter.

26. A method of producing a hybrid plant which, when pollinated will produce fruit with seed of a diminished size or very little number of seed comprising:

pollinating a parent plant which has been transformed or which ancestor thereof has been transformed with a first DNA sequence which encodes a first gene product which is capable of rendering a non-toxic substance cytotoxic to a cell of a plant said DNA sequence operably linked to a seed specific promoter; and with a second parent plant which has been transformed or whose ancestor has been transformed with a second DNA sequence which encodes a second gene product which is a non-toxic substance or encodes a second gene product which is capable of converting a substance endogenous to a plant cell to a non-toxic substance, said DNA sequence operably linked to a seed specific promoter, and said nontoxic substance one which is made cytotoxic by said first gene product.

27. The expression construct of claim 26 wherein said first DNA sequence encodes indole acetamide hydrolase (IamH), and wherein said second DNA sequence encodes indole acetamide synthase (IamS).

* * * * *